(12) United States Patent
Meshulach et al.

(10) Patent No.: US 7,684,048 B2
(45) Date of Patent: Mar. 23, 2010

(54) SCANNING MICROSCOPY

(75) Inventors: Doron Meshulach, Ramat-Gan (IL); Haim Feldman, Nof-ayalon (IL)

(73) Assignee: Applied Materials Israel, Ltd., Rehovot (IL)

( * ) Notice: Subject to any disclaimer, the term of this patent is extended or adjusted under 35 U.S.C. 154(b) by 537 days.

(21) Appl. No.: 11/559,741

(22) Filed: Nov. 14, 2006

(65) Prior Publication Data
US 2007/0109546 A1 May 17, 2007

Related U.S. Application Data

(60) Provisional application No. 60/736,983, filed on Nov. 15, 2005, provisional application No. 60/736,645, filed on Nov. 15, 2005, provisional application No. 60/736,646, filed on Nov. 15, 2005.

(51) Int. Cl.
*G01B 11/02* (2006.01)
(52) U.S. Cl. ....................... 356/511; 356/495
(58) Field of Classification Search ............. 356/495, 356/511, 512, 237.2
See application file for complete search history.

(56) References Cited

U.S. PATENT DOCUMENTS

| | | | |
|---|---|---|---|
| 3,013,467 A | 12/1961 | Minsky | |
| 4,953,188 A | 8/1990 | Siegel et al. | |
| 5,241,364 A | 8/1993 | Kimura | |
| 5,355,252 A * | 10/1994 | Haraguchi | 359/369 |
| 6,028,306 A | 2/2000 | Hayashi | |
| 6,248,988 B1 | 6/2001 | Krantz | |
| 6,288,382 B1 | 9/2001 | Ishihara | |
| 6,429,897 B2 | 8/2002 | Derndinger et al. | |
| 6,614,526 B1 | 9/2003 | Engelhardt | |
| 6,674,522 B2 | 1/2004 | Krantz et al. | |
| 6,809,808 B2 * | 10/2004 | Feldman et al. | 356/237.1 |
| 6,825,454 B2 | 11/2004 | Czarnetzki et al. | |
| 6,853,475 B2 * | 2/2005 | Feldman et al. | 359/285 |
| 7,053,395 B2 * | 5/2006 | Feldman et al. | 250/559.45 |
| 2003/0156280 A1 | 8/2003 | Reinhorn | |
| 2003/0179369 A1 * | 9/2003 | Feldman et al. | 356/237.2 |
| 2004/0075068 A1 * | 4/2004 | Feldman et al. | 250/559.45 |
| 2004/0080740 A1 * | 4/2004 | Feldman et al. | 356/237.2 |
| 2005/0225849 A1 | 10/2005 | Gouch | |

OTHER PUBLICATIONS

C. Thomas Larson et al., Bright field-bright future: Material defect detection with a laser scanning system, Solid State Technology, Sep. 1997, 7pp.

(Continued)

*Primary Examiner*—Patrick J Connolly
(74) *Attorney, Agent, or Firm*—Sonnenschein Nath & Rosenthal LLP (57) ABSTRACT

Apparatus for imaging a surface, including scanning optics, which are configured to scan and focus one or more traveling beams onto the surface so as to form one or more traveling spots thereon. The apparatus also includes collection optics, which are arranged to collect radiation scattered from the one or more traveling spots and to focus the radiation to form one or more image spots traveling along a line. The apparatus also has a detecting assembly, which consists of a detector which is configured to generate a signal in response to the one or more traveling image spots, and a detector entry port interposed between the collection optics and the detector, which is coincident with the line. The apparatus also includes phase and/or polarization altering elements for the traveling beams.

14 Claims, 7 Drawing Sheets

OTHER PUBLICATIONS

C.J. Koester, Scanning Mirror Microscope with Optical Sectioning Characteristics: applications in ophthalmology, published in Applied Optics, vol. 19, Jun. 1, 1980, pp. 1749-1757.

C.J.R. Sheppard et al., confocal microscopes with slit apertures, published in Journal of Modern Optics, vol. 35, No. 7, 1988, pp. 1169-1185.

* cited by examiner

SCANNING MICROSCOPY

CROSS REFERENCE TO RELATED APPLICATIONS

This application claims the benefit of U.S. Provisional Patent Application 60/736,983, filed Nov. 15, 2005, U.S. Provisional Patent Application 60/736,645, filed Nov. 15, 2005 and U.S. Provisional Patent Application 60/736,646, filed Nov. 15, 2005, which is are incorporated herein by reference.

FIELD OF THE INVENTION

The present invention relates generally to imaging an object, and specifically to imaging the object by scanning it with one or more sources of radiation, typically for the purpose of wafer and/or mask inspection.

BACKGROUND OF THE INVENTION

In production of a semiconductor die, imaging of the wafer upon which the dice are formed is an integral part of the fabrication process, and images are typically generated for many stages of the fabrication process. Typically, the wafer images are used for the purpose of inspection and/or quality control of the specific stages. One of the methods used to produce the images is to scan the wafer, and form the scanned images, and/or determine characteristics of the section of the wafer being scanned, from radiation returning from the section. The scanning process is relatively time-consuming, and methods for reducing the scanning time, while maintaining the quality of the received signals, are well known in the semiconductor art. One such method is to use apparatus that performs multiple scans simultaneously. A number of other methods and techniques have also been used for enhancing the production of the image of a scanned object. The references below describe some of these methods and techniques.

U.S. Pat. No. 5,355,252 to Haraguchi, whose disclosure is incorporated herein by reference, describes a scanning laser microscope using a single beam.

U.S. Pat. No. 6,674,522 to Krantz et al., whose disclosure is incorporated herein by reference, describes an optical technique for inspecting photomasks. The techniques are based on multiple modified radiation collection techniques.

U.S. Pat. No. 6,853,475, to Feldman et al., whose disclosure is incorporated herein by reference, describes a method for producing multiple optical beams which are scanned across the surface of a wafer. The method uses an acousto-optical device wherein multiple traveling lenses are generated, each lens forming a respective traveling beam which is focused onto, and which is scanned over, the wafer surface.

An article entitled "Bright field-bright future: Material defect detection with a laser scanning system," by Larson et al., published in Sep. 1997 in *Solid State Technology*, is incorporated herein by reference. The article describes splitting a single laser beam into two correlated beams. The two beams irradiate a surface, and the returning radiation is combined into one beam. The recombined beam provides information on the surface. The system uses a differential interference contrast (DIC) technique, first described by Nomarski et al. in *Rev. Metallurgie* L11, 121, 1955. In DIC the prism used to split the beam is a Wollaston prism, or a Nomarski prism.

Basic confocal microscopy principles were described in U.S. Pat. No. 3,013,467, to Minsky, whose disclosure is incorporated herein by reference. In a confocal microscope, a light beam is focused to a spot in the object plane, and this spot is imaged onto a small circular aperture (often a pinhole) placed in front of a detector. Confocal microscopy improves the discrimination of objects in the focal plane compared with those not in the plane.

In articles titled "Scanning mirror microscope with optical sectioning characteristics: applications in ophthalmology" by C. J. Koester, published in *Appl. Opt.*, 19, pgs 1749-1757, 1980, and "Confocal Microscopes with slit apertures" by C. J. R. Sheppard et al., published in *J. Mod. Opt.* 35, pgs 1169-1185 (1988), the use of a slit ("one-dimensional confocal") instead of a small circular aperture is described. Both articles are incorporated herein by reference. The use of a slit source with a slit aperture allows a larger signal to be detected, compared with a circular aperture with a diameter of the size of the slit width.

U.S. patent application Ser. No. 2005/0225849 to Gouch, whose disclosure is incorporated herein by reference, describes a confocal microscope having a slit source. The slit source is focused onto an object, and radiation from the object is focused onto a linear array of detectors.

U.S. Pat. No. 5,241,364 to Kimura, whose disclosure is incorporated herein by reference, describes a confocal phase contrast scanning microscope. The optics of the microscope includes an annular phase plate, via which a collimated beam is passed, before being focused to a point on an object. Light from the object is focused onto the entrance of a fiber optic, which transfers the received light to a detector. Scanning is performed by mechanically moving the optics and the object independently.

In an article titled "Tandem-scanning reflected-light microscope" by Petran et al., published in *J. Opt. Soc. Am.*, 58, pgs 661-664 (1968), whose disclosure is incorporated herein by reference, methods are proposed to allow simultaneous detection of signals from a large number of apertures in a scanning confocal microscope. The methods include using aperture arrays and Nipkow discs.

Other configurations of scanning confocal microscopes for inspection applications have been proposed. Examples are provided in U.S. Pat. No. 6,248,988 to Krantz, U.S. Pat. No. 6,429,897 to Derndinger et al., and U.S. patent application Ser. No. 2003/0156280 to Reinhorn, all of whose disclosures are incorporated herein by reference.

SUMMARY OF THE INVENTION

In embodiments of the present invention, a scanning microscope comprises an element, typically an acousto-optic (AO) element, which generates a multiplicity of traveling beams. The traveling beams are focused to spots at a surface being inspected, and returning radiation from the surface is imaged and detected at an array of detectors. The characteristics of the image may be improved by introducing one or more image enhancing elements into the optics irradiation and collection path.

In one embodiment, the image enhancing element comprises a detector assembly having a one-dimensional entry port. The entry port may comprise an element separate from the detectors, and is typically a slit positioned before the detectors, which are implemented as a one-dimensional linear array. Alternatively, the entry port may comprise the front surface of the detectors, in which case the detectors are also implemented as a one-dimensional array. Further alternatively, the detector assembly may comprise detectors coupled to first ends of fiber optics, the second ends of the fiber optics being configured as the one-dimensional entry port. Hereinbelow, unless otherwise stated, the entry port is assumed to be a slit.

The slit is aligned parallel with the traveling direction of the spots, and with the detectors, and dimensions of the slit and its position are set so that in a direction orthogonal to the slit, confocal effects are introduced, whereas in the slit direction, normal imaging takes place. Introduction of a one-dimensional slit reduces depth discrimination while relaxing the auto-focus requirements of the system, compared to a confocal two-dimensional circular aperture.

In an alternative embodiment, the image enhancing element comprises a Wollaston, Nomarski, or equivalent prism followed by an analyzer. The prism divides each of the traveling beams into two orthogonally polarized traveling beams, the beams being angularly displaced one from the other. The two beams are focused onto the surface being inspected, and the returning radiation is combined in the analyzer before being focused onto the detectors. Phase information of the surface is thus converted into different intensity levels at the detectors, and the different intensity levels enhance the visibility of aspects of the surface such as edges.

In a further alternative embodiment, the image enhancing element comprises an annular phase plate followed by an annular aperture or mask. The plate and the aperture (or mask) operate to form the microscope into a phase contrast microscope, and are positioned at appropriate entrance and exit pupils of the microscope so that their operation is not affected by the traveling beams.

In other disclosed embodiments of the present invention, two or more of the enhancing elements described above are incorporated into one scanning microscope. The advantages of each of the different enhancing elements are incorporated into the one microscope, without negatively affecting each other.

The present invention will be more fully understood from the following detailed description of the embodiments thereof, taken together with the drawings, a brief description of which follows.

DETAILED DESCRIPTION OF EMBODIMENTS

Figure 1A:
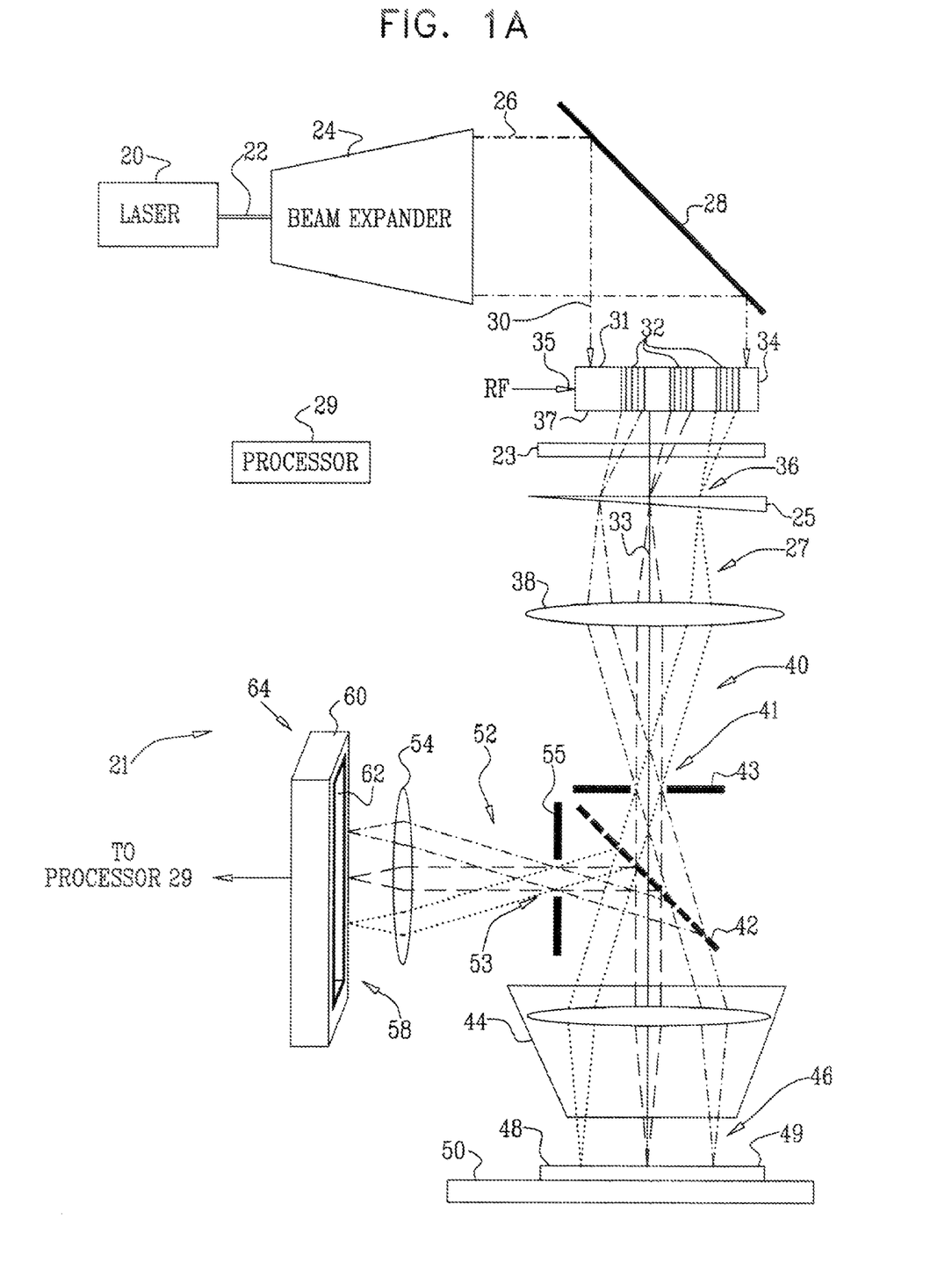
FIGS. 1A and 1B are schematic diagrams of a scanning microscope, according to an embodiment of the present invention.
Figure 1B:
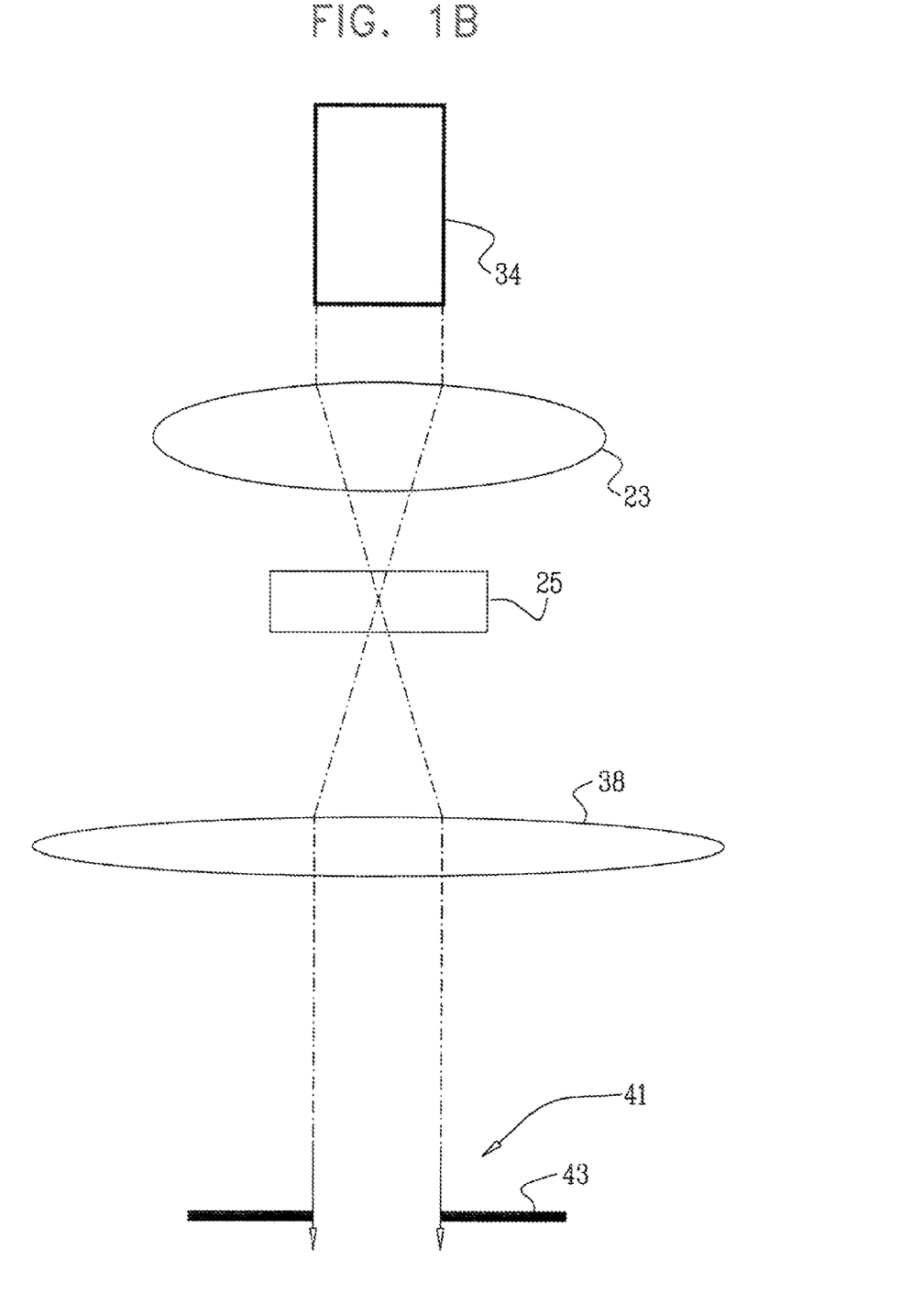

Reference is now made to FIG. 1A, which is a schematic diagram of a scanning microscope 21, and to FIG. 1B, which is a schematic side view of elements of the microscope, according to an embodiment of the present invention. Microscope 21 comprises a laser 20 which radiates a beam of coherent radiation 22 to a beam expander 24. Typically, laser 20 is selected to emit optical radiation at a wavelength in a region of the electromagnetic spectrum between and including far infra-red and deep ultra-violet (DUV), although it will be understood that the principles of the present invention apply equally to other wavelengths of the spectrum. Beam expander 24 generates an expanded collimated radiation beam 26 which reflects from a plane mirror 28 as a collimated radiation beam 30. A processor 29 operates elements of scanning microscope 21.

An acousto-optic (AO) element 34 receives beam 30 at a first surface 31 of the AO element, the first surface acting as a radiation input surface. Processor 29 generates a radio-frequency (RF) signal, with which it drives AO element 34 via an RF input port 35 coupled to the AO element. The RF signal is in the form of variable frequency pulses, or "chirps," each of which generates planar traveling acoustic waves in AO element 34. The planar traveling waves have varying wavelengths corresponding to the variable frequencies of the chirp. The waves act as traveling diffraction gratings 32 having variable spacing, and the gratings operate as cylindrical lenses which focus incoming beam 30, via a second surface 37 of the AO element acting as a radiation output surface. A cylindrical lens 23 focuses the converging beams from element 34 to a series of traveling focused spots 36, which are approximately collinear. A wedge-shaped prism 25, positioned at spots 36, receives the focused beams, and diverts the beams to respective diverging conical beams 27, the axes of each of the conical beams being approximately parallel to an axis 33 of microscope 21. A scanning lens 38 converts diverging beams 27 to a series of collimated beams 40. Collimated beams 40 pass through a pupil 41, and traverse a beam splitter 42 to an objective 44. Optionally, a stop 43 is positioned at pupil 41, the pupil acting as an exit pupil for lens 38, and as an entrance pupil for objective 44. (FIG. 1A and FIG. 1B show front and side views of elements 34, 23, 25, 38, and 43, and beam paths through the elements.)

Radiation exiting from splitter 42 is focused by objective 44 to a series of traveling spots 46 on a surface 48, the traveling spots typically traveling along an approximate straight line in the surface. In FIG. 1A the approximate straight line along which the points move is in the plane of the paper. Surface 48 is typically the upper surface of a wafer 49 which is being inspected by microscope 21. Typically, the number of spots 46 on surface 48 at any one time is from approximately three to approximately ten. However, the number of spots may vary from this range; it will be appreciated that the actual number on the surface at any one time is set by the rate of repetition of the RF chirps and the speed of the traveling waves in AO element 34.

Radiation scattered from spots 46 is collected by objective 44, and traverses generally the same path as the incoming radiation from splitter 42. In the specification and in the claims, scattered radiation is assumed to include radiation that is reflected. Objective 44 collimates the collected radiation, and the collimated beams from the objective are diverted by beam splitter 42 as a set of traveling collimated beams 52.

Beams 52 pass through a pupil 53, which is effectively a mirror image of pupil 41, and enter a converging lens 54. Optionally, a stop 55 is placed at pupil 53, which acts as an exit pupil for objective 44 and as an entrance pupil for lens 54. Lens 54 focuses traveling beams 52 to a linear series of substantially circular spots 58, at the focal plane of lens 54. A detecting assembly 60 includes a detector entry port 62, which is a linear substantially one-dimensional port allowing passage of radiation, and which is positioned at the focal plane of lens 54. Assembly 60 also includes a detector 64. Different embodiments of assembly 60 are described in more detail with reference to FIG. 2 below.

Radiation from spots 58 traverses port 62, and is received by detector 64. In response, detector 64, typically comprising a linear array of charged coupled detectors (CCDs) or photomultiplier tubes (PMTs), generates respective signals according to the intensity of the received radiation. Processor 29 receives the signals and analyzes them to determine characteristics of the regions of surface 48 generating the radiation.

Those with ordinary skill in the art will appreciate that the order of elements described above for microscope 21 is not unique, and that other arrangements of the elements may be made, giving substantially the same results as those described above; such rearrangements may require changes in elements used. For example, in one embodiment of the present invention, splitter 42 is positioned before pupil 41, causing pupil 53 to substantially coincide with pupil 41, so that one of stops 43 or 55 becomes superfluous. Other rearrangements of elements of microscope 21 will be apparent to those skilled in the art, and all such rearrangements are assumed to be included within the scope of the present invention.

Figure 2:
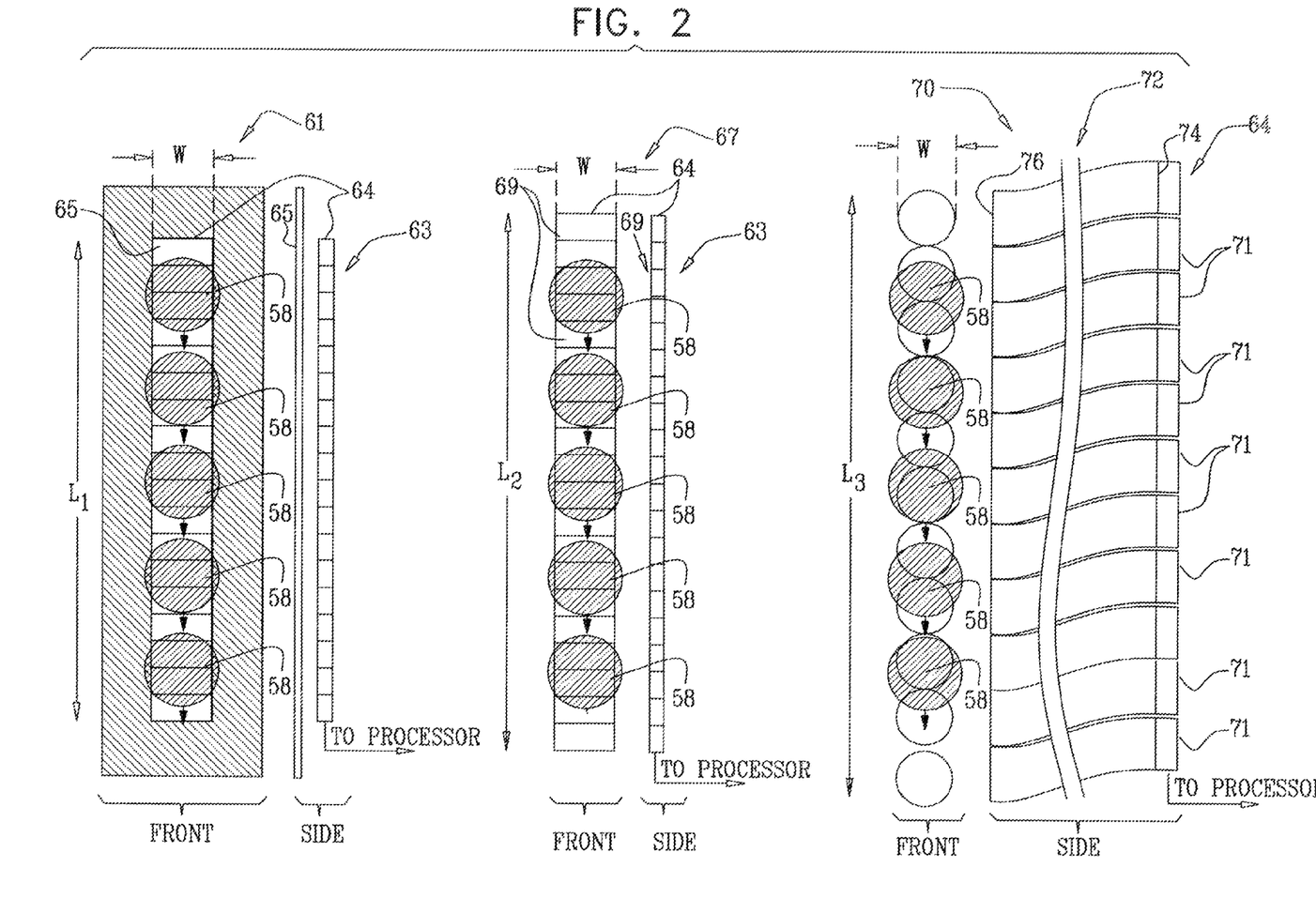
FIG. 2 is an enlarged schematic diagram of detecting assemblies used in the microscope of FIGS. 1A and 1B, according to an embodiment of the present invention.

FIG. 2 is a schematic diagram of three examples of detecting assembly 60, according to embodiments of the present invention. The three examples are each shown with schematic front and side views, and except where otherwise stated, each example is assumed to use a substantially similar detector 64 comprising a linear array of rectangular detecting elements 63.

In a first example 61, assembly 60 comprises a linear slit 65 acting as port 62, behind which is positioned detector 64. A length $L_1$ of slit 65 is set so that no detector elements are shielded from radiation of spots 58. Slit 65 is configured to have a width W approximately equal to a diameter D of spots 58. As is explained in more detail below, the actual width W is typically set according to the performance required of microscope 21 and the confocal effects generated by slit 65. As is known, spots 58 do not have sharp edges, and the diameter D referred to here is assumed to be the diameter of a circle within which approximately 90% of the energy of the radiation of the spot is found. Alternative methods known in the art for determining D, such as using a full width half maximum (FWHM) measure, or a value at which the spot intensity falls to a fraction such as $$\frac{1}{e^2}$$

of the central maximum intensity, may be used. All such methods are assumed to be included within the scope of the present invention.

By configuring circular spots 58 to traverse linear slit 65, rather than a circular aperture as in prior art confocal microscopes, embodiments of the present invention combine advantageously the properties of confocal and non-confocal systems. In a direction orthogonal to slit 65, the confocal properties preponderate; in a direction parallel to the slit, the non-confocal properties preponderate.

Typical values for W are in a range between approximately 0.5D and approximately 2D. The value of W affects both the depth of field of microscope 21, and its auto-focus requirements. A narrow slit provides high depth discrimination, and requires relatively restricted auto-focusing; a wide slit provides low depth discrimination, and requires relatively relaxed auto-focusing. Embodiments of the present invention typically set the value of W to take this dependence into account. Thus, by setting W to be approximately 0.5D, microscope 21 has a small depth of field and a correspondingly narrow range within which processor 29 is able to satisfactorily auto-focus; by setting W to be approximately 2D, microscope 21 has a relatively large depth of field and processor 29 has a correspondingly large range within which it is able to satisfactorily auto-focus.

In a second example 67, assembly 60 comprises only detector 64, which is configured to have a width W and a length $L_2$. $L_2$ is set so that all radiation from spots 58 is received by the detector. Width W is set substantially as described for width W in example 61, and the description of the properties of W given therein also applies. In example 67, front faces 69 of elements 63 of detector 64 act as entry port 62.

In a third example 70, assembly 60 comprises detector elements 71 acting as detector 64, and fiber optic cables 72. Elements 71 are generally similar to elements 63, but may, as shown in FIG. 2, be separate elements. Elements 71 are coupled to cables 72 at first ends 74 of the cables, and second ends 76 of cables act as entry port 62. Second ends 76 are arranged in a line, which is configured to have a width W and a length $L_3$. $L_3$ is set so that all radiation from spots 58 is incident on ends 76. Width W is set substantially as described for width W in example 61, and the description of the properties of W given therein also applies.

Those having ordinary skill in the art will be aware of techniques other than the three examples given here for forming detecting assembly 60, and all such techniques are assumed to be included within the scope of the present invention.

Figure 3:
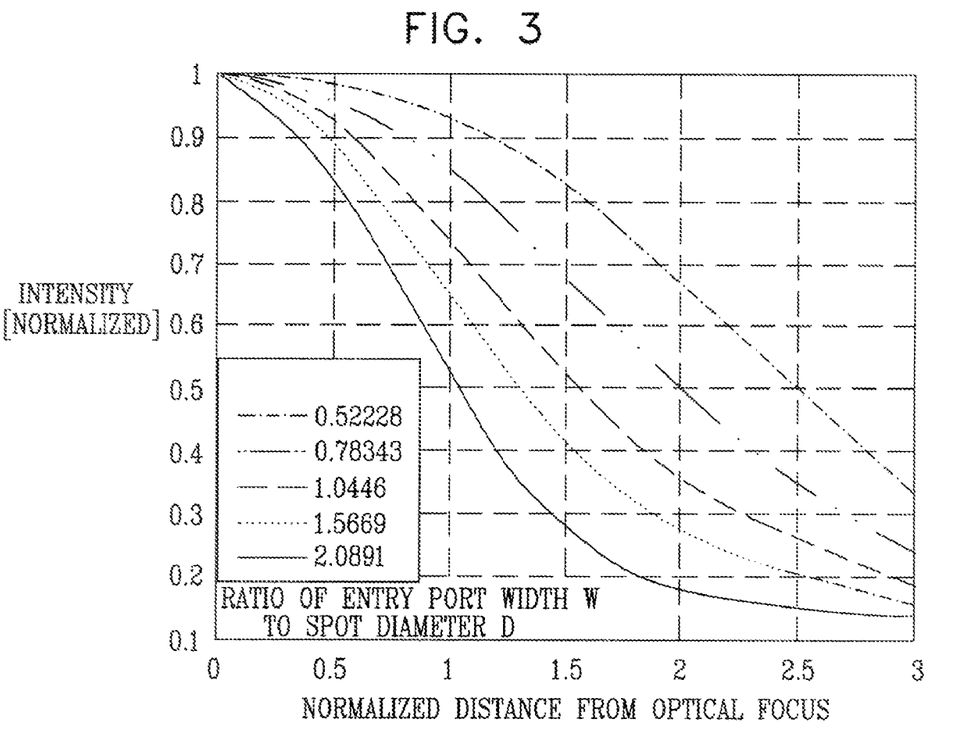
FIG. 3 shows simulated graphs of intensity vs. amount of defocusing, according to an embodiment of the present invention

FIG. 3 shows simulated graphs of intensity vs. amount of defocusing, for different values of width W of entry port 62 (FIGS. 1A and 2), according to an embodiment of the present invention. The vertical axis of the graphs plots normalized intensities of radiation received at entry port 62. The horizontal axis plots normalized distances of entry port 62 from the theoretical focus plane of lens 54, i.e., a defocus distance. The graphs illustrate the effects described above with respect to FIG. 2, i.e., that for a given defocus distance, as the width W of port 62 decreases, the intensity ratio at detector 64 also decreases, so that microscope 21 has a smaller depth of field, and consequently an increased depth discrimination.

Figure 4:
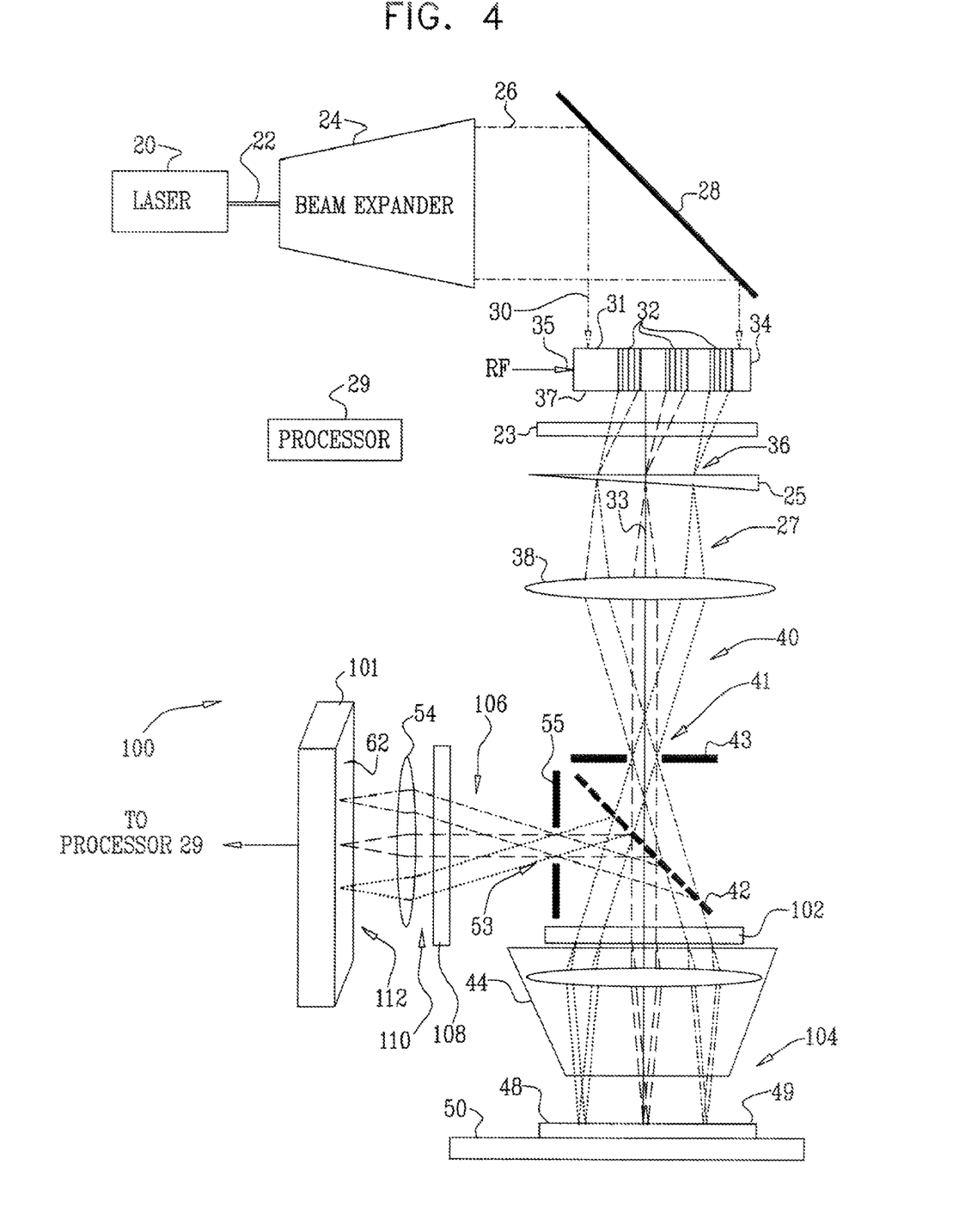
FIG. 4 is a schematic diagram of a scanning microscope, according to an alternative embodiment of the present invention.

FIG. 4 is a schematic diagram of a scanning microscope 100, according to an alternative embodiment of the present invention. Apart from the differences described below, the operation of microscope 100 is generally similar to that of microscope 21 (FIGS. 1A and 1B), such that elements indicated by the same reference numerals in both microscopes 100 and 21 are generally identical in construction and in operation. In place of detecting assembly 60, a detector 101 is used. Detector 101 is typically generally similar to detector 64 described above with reference to example 61 (FIG. 2), although it may not necessarily have dimensions that give the detector confocal properties. In microscope 100 a Wollaston, Nomarski, or equivalent prism 102, herein termed a polarizing beam splitter prism, is positioned between beam splitter 42 and objective 44. Polarizing beam splitter prisms are well known in the optical art, and descriptions of them are provided in more detail in references given in the Background of the Invention. As described therein, a polarizing beam splitter prism separates an incoming radiation beam into two plane polarized beams having orthogonal planes of polarization. There is an angular separation between the two beams. In microscope 100, beams 40 are plane polarized if laser 20 emits beam 22 as plane polarized radiation. If beam 22 is not plane polarized, then one or more elements before prism 102 are adapted to plane polarize beams 40; alternatively, a polarizer is added to microscope 100 to form beams 40 into plane polarized beams.

Prism 102 is aligned so that its axis is 45° to the plane of polarization of beams 40, in order that the two plane polarized beams emitted by the prism have approximately equal intensities. Thus, prism 102 separates each of incoming beams 40 into a pair of orthogonal plane polarized beams. Each pair of beams is focused by objective 44 to a pair of spots 104, in contrast to microscope 21, wherein one beam 40 is focused to one spot 46. Prism 102 is constructed so that the two beams it outputs subtend an angle of the order of 100 μrad with each other, typically so that each pair of spots 104 is separated by approximately one spot diameter.

Objective 44 collects radiation from pairs of spots 104, and conveys the collected radiation to prism 102, along paths which are substantially the reverse of the paths of the beams exiting from the prism. Prism 102 consequently combines the returning radiation from each pair of spots 104 into single beams 106 (only the central lines of the beams are shown), each single beam consisting of a pair of orthogonally polarized overlapping beams. An analyzer 108, aligned at 45° to the two polarization directions of the radiation of each of the beams 106, acts to coherently interfere between the two polarizations to form sets of coherent beams 110, each beam 110 being the result of the interference of its pair of beams.

Substantially as described above for microscope 21, lens 54 focuses beams 110 to a set of traveling spots 112 on detector 101. It will be understood that the intensity variations registered by detector 101 are the result of the beam interference generated by analyzer 108.

It will also be appreciated that microscope 100 functions as a scanning differential interference contrast microscope, so that, for example, slope changes in surface 48 that may be poorly detected, or not detected at all, using a normal microscope are typically well detected in microscope 100. Such slope changes may be caused by a variety of features on surface 48, including edges of such features, as well as defects on the surface.

Figure 5:
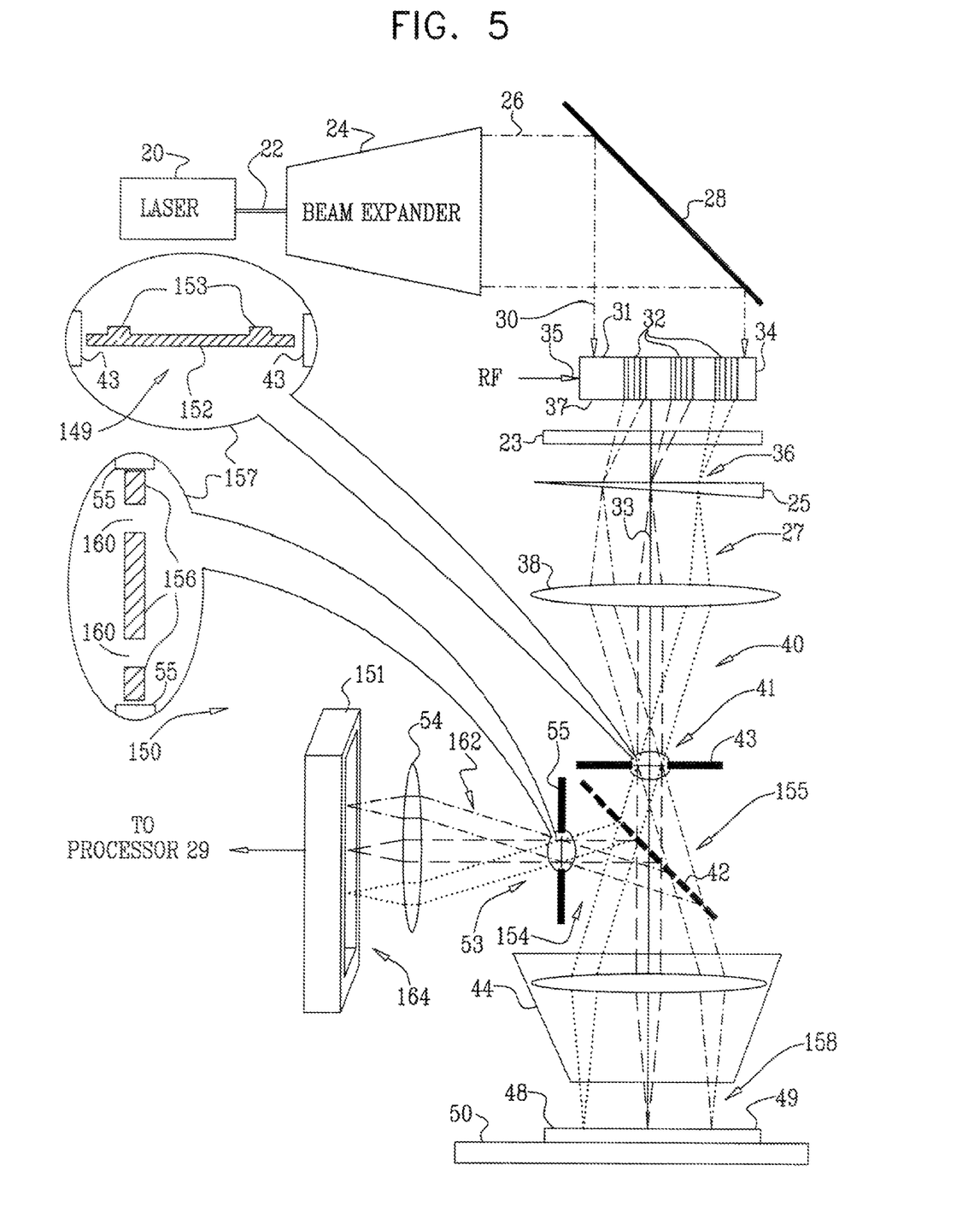
FIG. 5 is a schematic diagram of a scanning microscope, according to a further alternative embodiment of the present invention.

FIG. 5 is a schematic diagram of a scanning microscope 150, according to a further alternative embodiment of the present invention. Apart from the differences described below, the operation of microscope 150 is generally similar to that of microscope 21 (FIGS. 1A and 1B), such that elements indicated by the same reference numerals in both microscopes 150 and 21 are generally identical in construction and in operation. In place of detecting assembly 60, a detector 151 is used. Detector 151 is typically generally similar to detector 64 described above with reference to example 61 (FIG. 2), although it may not necessarily have dimensions that give the detector confocal properties. In microscope 150 a phase plate 152 is positioned at exit pupil 41 of lens 38. For clarity, phase plate 152 is shown enlarged and displaced from pupil 41 in FIG. 5, in an inset 157. Phase plate 152 has a circular ring 153 which is configured to generate a phase shift of $$\frac{\pi}{2}$$

between radiation passing through the ring and radiation passing through the remainder of the plate. It will be understood that the phase shift introduced may be by ring 153 acting as a phase retarder, or as a phase advancer. By way of example, hereinbelow ring 153 is assumed to produce a phase retardation of $$\frac{\pi}{2}.$$

In some embodiments of the present invention, phase plate 152 includes an attenuating region 149 which attenuates a portion of the beam traversing the phase plate. Region 149 may be positioned in ring 153, and/or in a remaining portion of the plate, as described in more detail below.

The radiation having the two phases, shown schematically in FIG. 5 as beams 155, traverses beam splitter 42 and is focused by objective 44 to form traveling spots 158 on surface 48. The operation of beam splitter 42 and objective 44 is generally as described above with reference to FIG. 1A, and except for the phase shift introduced by plate 152, spots 158 are generally similar to spots 46.

Returning radiation from spots 158 is collected by objective 44 and is reflected by beam splitter 42 as radiation 154, substantially as described above for the operation of microscope 21. An annular aperture mask 156 is positioned so that it and phase plate 152 are at conjugate foci of objective 44, and also so that the annular aperture is approximately at entrance pupil 53 of lens 54, between the lens and splitter 42. (For clarity, mask 156 is shown enlarged and displaced from pupil 53 in inset 157.) The width of an annulus 160 of aperture mask 156 is configured to be consistent with that of the width of ring 153. Annulus 160 constrains retarded and non-retarded radiation from spots 158 into the same path, to form beams 162. Beams 162 are focused by lens 54 onto detector 151, to form spots 164, generally as described above for spots 58. Alternatively, instead of mask 156 being configured as an annular aperture, the mask may be configured as an annular stop.

It will be understood that microscope 150 operates as a scanning phase contrast microscope, so that slope or phase features on surface 48 that would normally be undetectable with a normal microscope become detectable. In embodiments having attenuating region 149 in plate 152, the region is positioned with respect to mask 156, and the amount of attenuation the region provides is chosen, so that the attenuation enhances the phase contrast image generated by the plate-mask combination.

Returning to FIGS. 1A and 1B, it will be appreciated that scanning microscopes generally similar to microscope 21 may be implemented using scanning mechanisms other than the specific system described with reference to acousto-optic element 34. For example, instead of beam expander 24, mirror 28, AO element 34, lens 23, wedge 25, and lens 38, a scanning mechanism may comprise a beam multiplexer followed by a rotating mirror, the multiplexer and mirror being configured to provide multiple beams substantially similar to the series of parallel beams 40 described above.

It will also be appreciated that elements of the microscopes described above may be combined to form compound scanning microscopes. An example of such a combination is described in more detail below with reference to FIG. 6; all such combinations are assumed to be included within the scope of the present invention.

Figure 6:
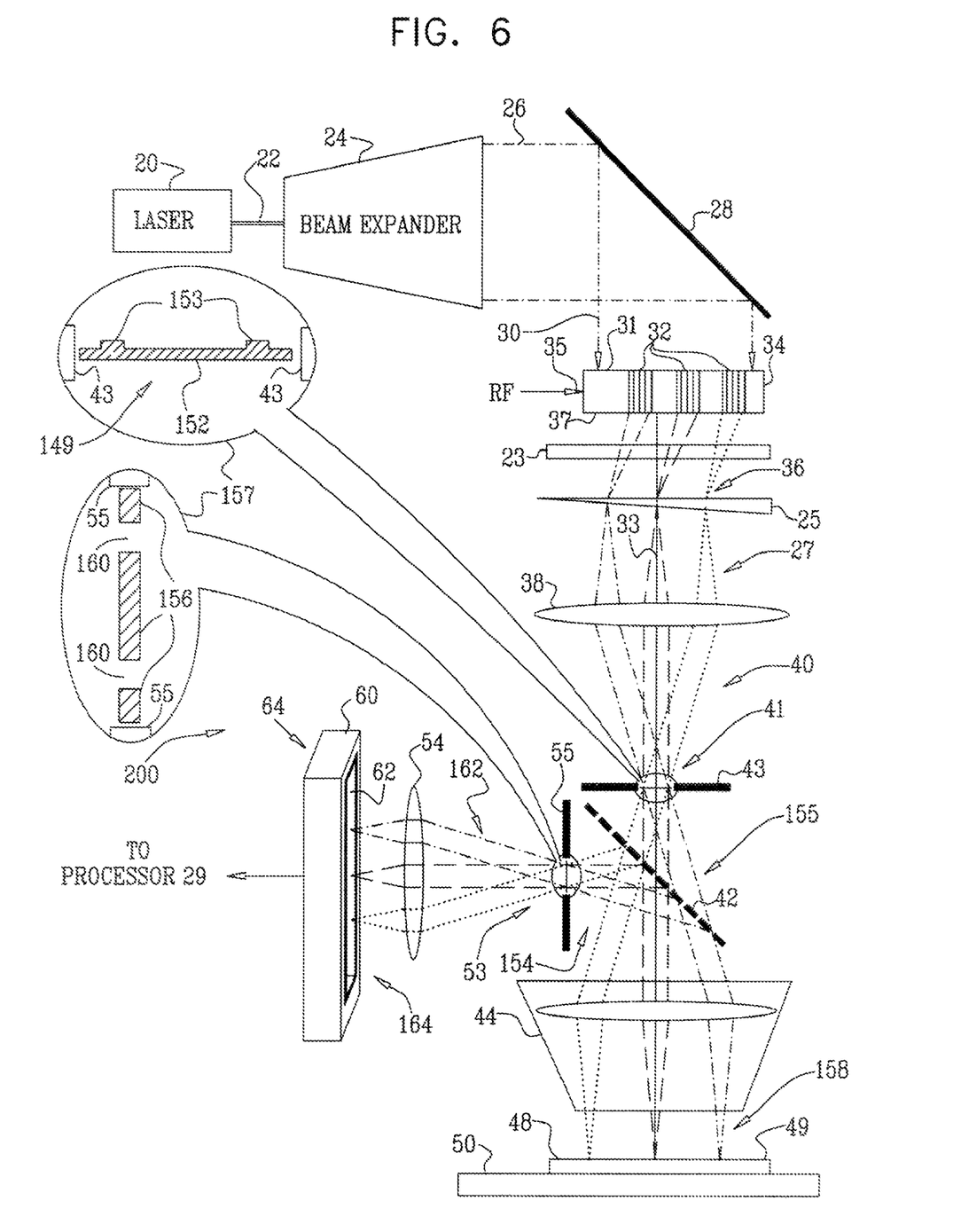
FIG. 6 is a schematic diagram of a scanning microscope, according to another alternative embodiment of the present invention.

FIG. 6 is a schematic diagram of a scanning microscope 200, according to another alternative embodiment of the present invention. Apart from the differences described below, the operation of microscope 200 is generally similar to that of microscopes 21 and 150 (FIGS. 1A, 1B and 5), such that elements indicated by the same reference numerals in microscopes 200, 150, and 21 are generally identical in construction and in operation. Microscope 200 uses phase element 152 and mask element 156 as used by microscope 150, as well as detecting assembly 60 as used by microscope 21. Thus, in the case of microscope 200, spots 164 are formed substantially as described above for microscope 150. However, assembly 60 acts on spots 164 as described above with reference to FIGS. 1A, 1B, and 2. It will be appreciated that the effects of the phase and mask elements, and of the slit assembly, are substantially independent of each other. The image detected by detector 64 is thus a phase contrast image, showing the slope or phase features described above for microscope 150; in addition, the image has the confocal advantages described above for microscope 21.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus for imaging a surface, comprising:
   an acousto-optic (AO) element having a radiation input surface and a radiation output surface, which is configured to receive a series of radio-frequency (RF) pulses and a radiation input at the radiation input surface and to generate in response thereto focused traveling beams from the radiation output surface;
   means for separating each of the traveling beams into one or more of (i) a plurality of phase-altered-traveling-beams or (ii) a plurality of orthogonal-polarized-traveling-beams;
   objective optics which are configured to focus the separated traveling beams onto the surface so as to form respective traveling spots thereon;
   collection optics, which are configured to (a) collect scattered radiation from the traveling spots, (b) perform one or more of (i) overlapping scattered radiation originating from one phase-altered-traveling-beam with scattered radiation originating from another phase-altered-traveling-beam or (ii) overlapping scattered radiation originating from one orthogonal-polarized-traveling-beam with scattered radiation originating from another orthogonal-polarized-traveling-beam and (c) to focus the scattered radiation to form respective image spots traveling along a line;
   a detector which is arranged to generate a signal in response to the respective image spots incident thereon;
   a detector entry port interposed between the collection optics and the detector, which is coincident with the line; and
   means for intercepting the scattered radiation and masking, from the detector, a portion of the scattered radiation collected by the collection optics.

2. Apparatus for imaging a surface, comprising:
   an acousto-optic (AO) element having a radiation input surface and a radiation output surface, which is configured to receive a series of radio-frequency (RF) pulses and a radiation input at the radiation input surface and to generate in response thereto focused traveling beams from the radiation output surface;
   a phase plate, which is arranged to incorporate a phase shift into a portion of each of the focused traveling beams, so as to form phase-altered-traveling-beams;
   objective optics which are configured to focus the phase-altered-traveling-beams onto the surface so as to form traveling spots thereon;
   collection optics, which are configured to collect scattered radiation from the traveling spots and to focus the scattered radiation to form respective image spots traveling along a line;
   a detector which is arranged to generate a signal in response to the respective image spots incident thereon;
   a detector entry port interposed between the collection optics and the detector, which is coincident with the line; and
   a mask, positioned to intercept the scattered radiation, and which is arranged to mask a portion of the scattered radiation from the detector.

3. The apparatus according to claim 2, wherein the AO element is configured to produce traveling lenses therein in response to the RF pulses, and wherein the traveling lenses generate the focused traveling beams.

4. The apparatus according to claim 2, wherein the phase plate comprises an annular ring which produces the phase shift.

5. The apparatus according to claim 4, wherein the mask comprises one of an annular opening and an annular stop.

6. The apparatus according to claim 5, wherein the annular ring has an annular-ring-width, and wherein the one of the annular opening and the annular stop has an annular-opening-width formed in response to the annular-ring-width.

7. The apparatus according to claim 1, wherein the phase shift comprises one of an advance of $$\frac{\pi}{2}$$

and a retardation pf $$\frac{\pi}{2}.$$

8. The apparatus according to claim 1, wherein the phase plate comprises an attenuating region which is positioned within the plate, in response to the mask, so as to attenuate a part of each of the one or more traveling beams.

9. Apparatus for imaging a surface, comprising:
   an acousto-optic (AO) element having a radiation input surface and a radiation output surface, and which is configured to receive a series of radio-frequency (RF) pulses and a radiation input at the radiation input surface and to generate in response thereto focused traveling beams from the radiation output surface;
   a first polarizing optic, which is arranged to separate each of the traveling beams into a pair of orthogonally-polarized-traveling-beams;
   objective optics which are configured to focus each pair of orthogonally-polarized-traveling-beams onto the surface so as to form respective pairs of traveling spots thereon;
   collection optics, which are configured to collect scattered radiation from the pairs of traveling spots and, for each pair, to focus the scattered radiation to form respective image spots traveling along a line;
   a detector which is arranged to generate a signal in response to the respective image spots incident thereon;

a detector entry port interposed between the collection optics and the detector, which is coincident with the line; and a second polarizing optic, positioned to intercept and polarize the scattered radiation.

10. The apparatus according to claim 9, wherein the AO element is configured to produce traveling lenses therein in response to the RF pulses, and wherein the traveling lenses generate the focused traveling beams.

11. The apparatus according to claim 9, wherein the first polarizing optic comprises a prism, and wherein the prism is arranged to receive and combine the scattered radiation from each pair of traveling spots into a single beam of two orthogonally polarized beams.

12. The apparatus according to claim 11, wherein the second polarizing optic comprises an analyzer which is aligned to cause the two orthogonally polarized beams to interfere.

13. A method for imaging a surface, comprising:

receiving, in an acousto-optic (AO) element having a radiation input surface and a radiation output surface, a series of radio-frequency (RF) pulses and a radiation input at the radiation input surface, and generating in response thereto focused traveling beams from the radiation output surface;

incorporating a phase shift into a portion of each of the focused traveling beams, so as to form phase-altered-traveling-beams;

focusing the phase-altered-traveling-beams onto the surface so as to form traveling spots thereon;

collecting scattered radiation from the traveling spots and focusing the scattered radiation to form respective image spots traveling along a line on a detector;

generating a signal in the detector in response to the respective image spots focused thereon;

positioning a detector entry port in proximity to the detector so that the port coincides with the line; and positioning a mask to intercept the scattered radiation, and masking a portion of the scattered radiation from the detector using the mask.

14. A method for imaging a surface, comprising:

receiving, in an acousto-optic (AO) element having a radiation input surface and a radiation output surface, a series of radio-frequency (RF) pulses and a radiation input at the radiation input surface, and generating in response thereto focused traveling beams from the radiation output surface;

separating each of the traveling beams into a pair of orthogonally-polarized-traveling-beams;

focusing each pair of orthogonally-polarized-traveling-beams onto the surface so as to form respective pairs of traveling spots thereon;

collecting scattered radiation from the pairs of traveling spots and, for each pair, focusing the scattered radiation to form respective image spots traveling along a line on a detector;

positioning a detector entry port in proximity to the detector so that the port coincides with the line; generating a signal in the detector in response to the respective image spots focused thereon; and positioning a polarizing optic to intercept and polarize the scattered radiation.

* * * * *